(12) United States Patent
Mauch

(10) Patent No.: US 10,463,424 B2
(45) Date of Patent: Nov. 5, 2019

(54) CATHETERS WITH INDEPENDENT RADIAL-EXPANSION MEMBERS AND ASSOCIATED DEVICES, SYSTEMS, AND METHODS

(71) Applicant: Medtronic Ardian Luxembourg S.a.r.l., Luxembourg (LU)

(72) Inventor: Kevin Mauch, Windsor, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 1196 days.

(21) Appl. No.: 14/203,826

(22) Filed: Mar. 11, 2014

(65) Prior Publication Data
US 2015/0257824 A1 Sep. 17, 2015

(51) Int. Cl.
A61B 18/14 (2006.01)
A61B 18/00 (2006.01)
A61N 7/00 (2006.01)

(52) U.S. Cl.
CPC ........... *A61B 18/1492* (2013.01); *A61B 2018/00214* (2013.01); *A61B 2018/00434* (2013.01); *A61B 2018/1475* (2013.01); *A61N 2007/003* (2013.01)

(58) Field of Classification Search
CPC .. A61B 2018/1464; A61B 2018/00267; A61B 2018/00214; A61B 2018/0016
See application file for complete search history.

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

CN 101547654 4/2012
CN 103118619 5/2013
(Continued)

OTHER PUBLICATIONS

International Search Report and Written Opinion for International Application No. PCT/US2015/019986, dated Jun. 12, 2015, 10 pages.
(Continued)

*Primary Examiner* — Michael F Peffley
*Assistant Examiner* — Bo Ouyang
(74) *Attorney, Agent, or Firm* — Medtronic Vascular, Inc. IP Legal Department

(57) ABSTRACT

A neuromodulation catheter includes an elongate shaft and a neuromodulation element operably connected to the shaft. The neuromodulation element includes an elongate support member and a plurality of bow springs operably connected to the support member. The individual bow springs are configured to independently expand radially outward from the support member when the neuromodulation element transitions from a low-profile delivery state to a deployed state at a treatment location within a body lumen. The individual bow springs include a distal leg and a proximal leg and carry an electrode and/or a transducer between their respective distal and proximal legs. The distal and proximal legs of the plurality of bow springs are longitudinally interdigitated. The plurality of bow springs is configured to urge the electrodes and/or the transducers into contact with an inner surface of a wall of the body lumen at a series of contact regions.

24 Claims, 10 Drawing Sheets

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele et al. |
| 5,865,787 A | 2/1999 | Shapland et al. |
| 5,893,847 A | 4/1999 | Kordis |
| 5,893,885 A | 4/1999 | Webster, Jr. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto et al. |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2001/0007939 A1 | 7/2001 | Fleischman |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danek et al. |
| 2004/0010289 A1 | 1/2004 | Biggs et al. |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0058598 A1* | 3/2006 | Esposito ............ A61B 18/1492 600/374 |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0271111 A1 | 11/2006 | Demarais et al. |
| 2007/0083194 A1 | 4/2007 | Kunis et al. |
| 2007/0129720 A1 | 6/2007 | Demarais et al. |
| 2007/0265687 A1 | 11/2007 | Deem et al. |
| 2008/0306499 A1* | 12/2008 | Katoh ............ A61B 17/320725 606/159 |
| 2008/0319513 A1 | 12/2008 | Pu et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0168739 A1 | 7/2010 | Wu et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0023088 A1 | 1/2011 | Ko et al. |
| 2012/0130289 A1 | 5/2012 | Demarais et al. |
| 2012/0130345 A1 | 5/2012 | Levin et al. |
| 2012/0172837 A1 | 7/2012 | Demarais et al. |
| 2013/0231659 A1* | 9/2013 | Hill .................... A61B 18/1492 606/41 |
| 2014/0088591 A1* | 3/2014 | Just ..................... A61B 5/0422 606/41 |

FOREIGN PATENT DOCUMENTS

| | | |
|---|---|---|
| WO | WO1994007446 | 4/1994 |
| WO | WO-1995025472 | 9/1995 |
| WO | WO1995031142 | 11/1995 |
| WO | WO-1997036548 | 10/1997 |
| WO | WO1998042403 | 10/1998 |
| WO | WO-1999/00060 | 1/1999 |
| WO | WO1999000060 | 1/1999 |
| WO | WO-2001022897 | 4/2001 |
| WO | WO-2001070114 | 9/2001 |
| WO | WO2003022167 | 3/2003 |
| WO | WO2003082080 | 10/2003 |

(56) References Cited

FOREIGN PATENT DOCUMENTS

| WO | WO-2005030072 | 4/2005 |
|---|---|---|
| WO | WO-2005041748 | 5/2005 |
| WO | WO-2005110528 | 11/2005 |
| WO | WO-2006041881 | 4/2006 |
| WO | WO2006084635 | 8/2006 |
| WO | WO2006105121 | 10/2006 |
| WO | WO-2007008954 | 1/2007 |
| WO | WO2007078997 | 7/2007 |
| WO | WO2008049084 | 4/2008 |
| WO | WO2015138617 | 9/2015 |

OTHER PUBLICATIONS

Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Miller, Reed, "Finding A Future For Renal Denervation With Better Controlled Trials." Pharma & Medtech Business Intelligence, Article # 01141006003, Oct. 6, 2014, 4 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2J05 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures" Third Edition, pp. 194-210 (2002).
Mount Sinai School of Medicine clinical trial for impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 : 484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension," New England Journal of Med, Aug. 2009, 361;9.
Luipold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimenda Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14;27-30.

(56) References Cited

OTHER PUBLICATIONS

Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months, Hypertension. 2011 ;57(5):911-917.
Symplicity HTN-2 Investigators, "Renal Sympathetic Denervation in Patients with Treatment-Resistant Hypertension (The Sympiicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care," [Brochure], Terumo Europe N.V., 2013, Europe, 3 pages.
"Neurotech Reports Announces Winners of Gold Electrode Awards." Neurotech business report, 2009. 1 page, <http://www.neurotechreports.com/pages/goldelectrodes09.html>.
"Quick. Consistent. Controlled, OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty For The Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al., "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension," U.S. Appl. No. 60/442,970, filed Jan. 29, 2003, 23 pages.
Gertner, Jon, "Meet The Tech Duo That's Revitalizing The Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

(56) References Cited

OTHER PUBLICATIONS

Hall, W. H., et al. "Combined embolization and percutaneous radiofrequency ablation of a solid renal tumor." *Am. J. Roentgenol*, 174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87:13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris. AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2;527-534 (2001).
Lee, S.J., et al. "Ultrasonic anergy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.et al., "Cryotherrnal ablation: Mechanism of tissue injury and current experience in the treatment of tachyarrhythmias." Progr Cardiovasc Dis, 41:481-498 (1999).
Maben, Tam et al., "First experience wiih endovascuiar ultrasound renal denervation for the treatment of resistant hyperierision." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hernodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid-80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol., vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haerrodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
European Search Report for European Application No. 13159256, dated Oct. 17, 2013, 6 pages.
Beale, et al., "Minimally Invasive Treatment for Varicose Veins: A Review of Endovenous Laser Treatment and Radiofrequency Ablation". Lower Extremity Wounds 3(4), 2004, 10 pages.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.
Opposition to European Patent No. 2465470, Granted Oct. 28, 2015, Date of Opposition Jul. 27, 2016, 34 pages.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

(56) References Cited

OTHER PUBLICATIONS

U.S. Appl. No. 11/363,867, filed Feb. 27, 2006, 70 pp.
U.S. Appl. No. 60/813,589, filed Dec. 29, 2005, 62 pp.
U.S. Appl. No. 60/852,787, filed Oct. 18, 2006, 112 pp.
Ureter, https://en.wikipedia.org/wiki/Ureter, Jun. 2016, 6 pp.

* cited by examiner

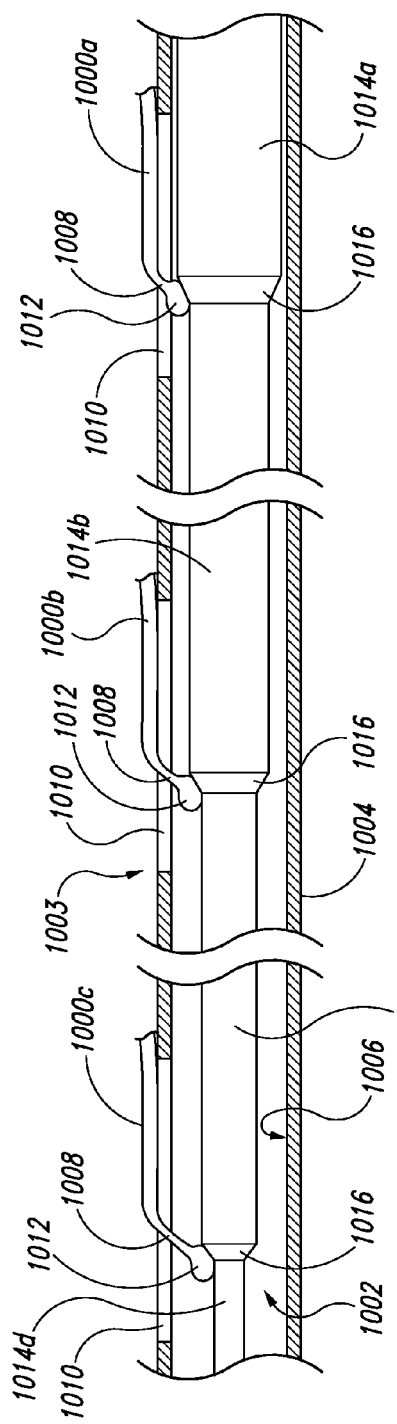
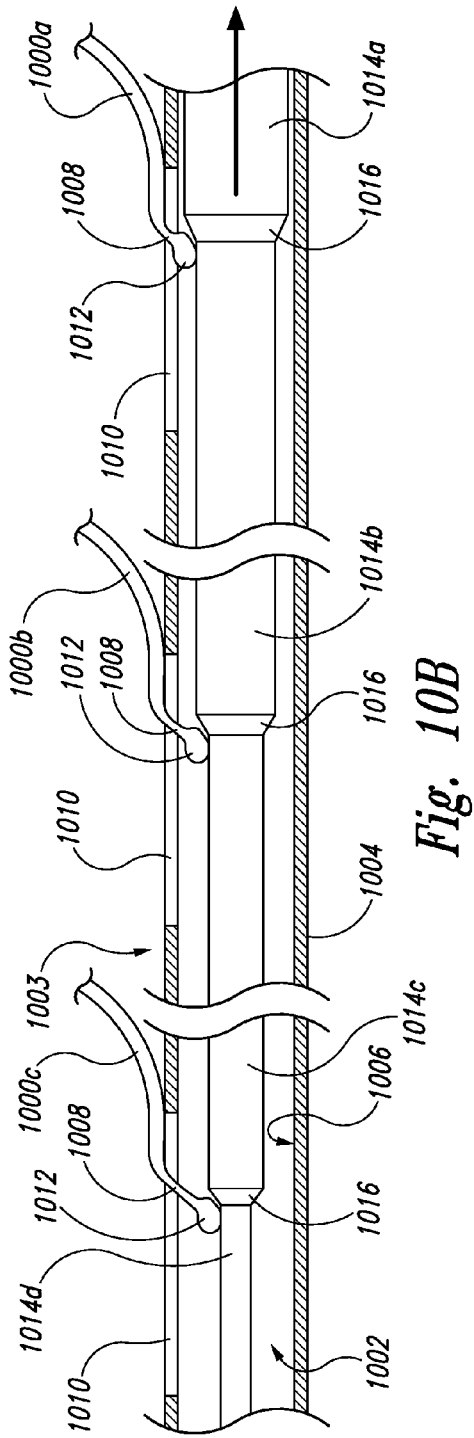

CATHETERS WITH INDEPENDENT RADIAL-EXPANSION MEMBERS AND ASSOCIATED DEVICES, SYSTEMS, AND METHODS

TECHNICAL FIELD

The present technology is related to catheters. In particular, at least some embodiments are related to neuromodulation catheters including neuromodulation elements configured to deliver energy to nerves at or near a treatment location within a body lumen.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS, in particular, has been identified experimentally and in humans as a likely contributor to the complex pathophysiologies of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

In FIG. 2A, the radial-expansion member is shown in a radially expanded state. In FIG. 2B, the radial-expansion member is shown in a radially constrained state.

In FIG. 3A, the radial-expansion member is shown in a radially expanded state. In FIG. 3B, the radial-expansion member is shown in a radially constrained state.

In FIG. 4A, the radial-expansion member is shown in a radially expanded state. In FIG. 4B, the radial-expansion member is shown in a radially constrained state.

In FIG. 7A, the therapeutic element is in a low-profile delivery state within a sheath. In FIG. 7B, the therapeutic element is shown in a first intermediate state as the therapeutic element transitions from the delivery state to a deployed state. In FIG. 7C, the therapeutic element is shown in a second intermediate state as the therapeutic element transitions from the first intermediate state to the deployed state. In FIG. 7D, the therapeutic element is shown in the deployed state.

FIGS. 10A and 10B are cross-sectional side views of a series of radial-expansion members and an associated segment of a support member of a therapeutic element of a catheter configured in accordance with another embodiment of the present technology. In FIG. 10A, the radial-expansion members are shown in radially constrained states. In FIG. 10B, the radial-expansion member are shown in radially expanded states.

DETAILED DESCRIPTION

Figures 1A, 1B:
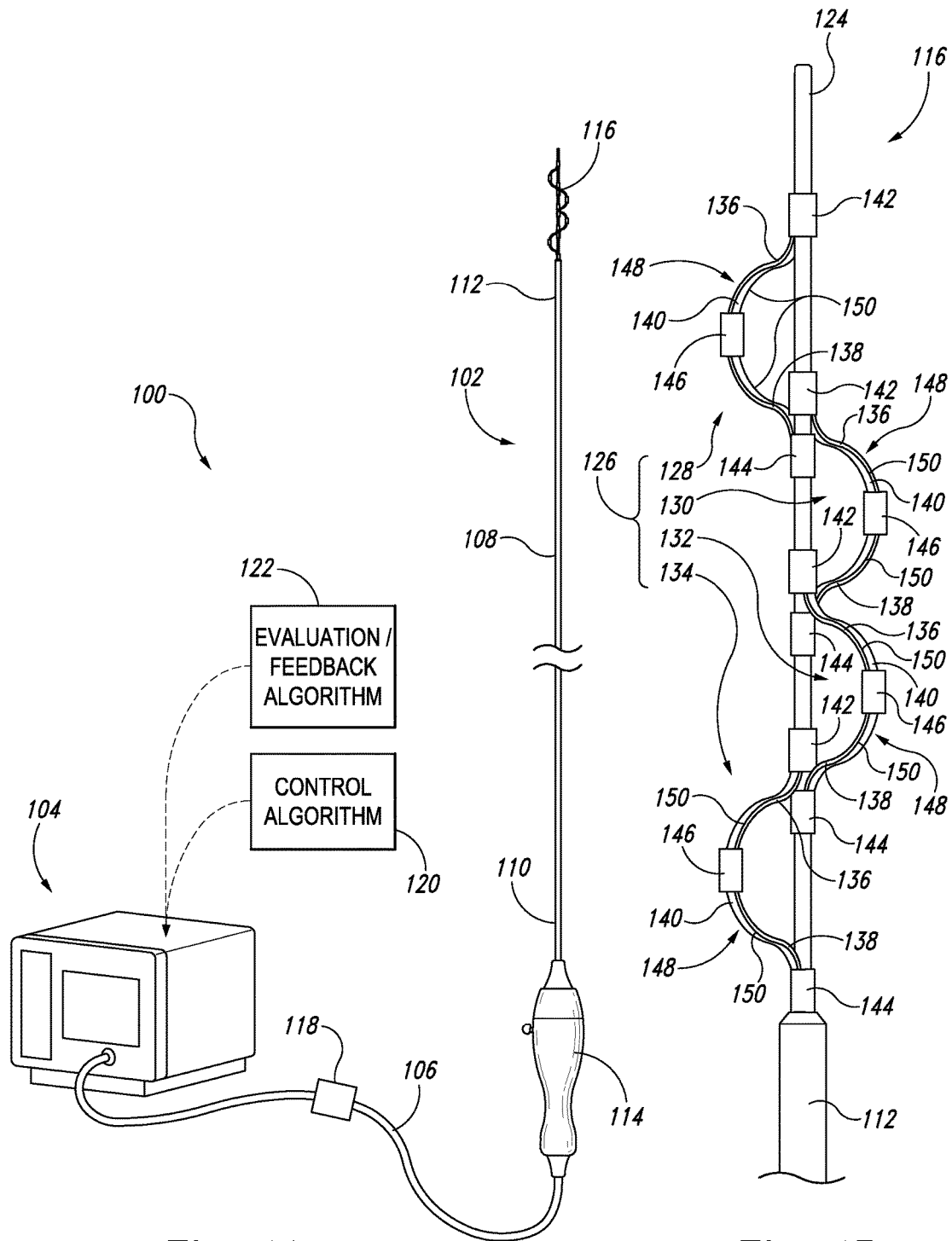
FIG. 1A is a perspective view of a system including a catheter, console and cable configured in accordance with an embodiment of the present technology. The catheter includes an elongated shaft and a therapeutic element operably connected to the shaft.
FIGS. 1B and 1C are an enlarged side view and an enlarged perspective view, respectively, of the therapeutic element shown in FIG. 1A.

The present technology is related to catheters, such as catheters including neuromodulation elements configured to deliver energy to nerves at or near a treatment location within a body lumen. More specifically, catheters configured in accordance with at least some embodiments of the present technology are expected to treat tissue (e.g., nerves) at or near treatment locations within geometrically irregular (e.g., curved and/or non-cylindrical) segments of body lumens in a reliable and consistent manner. With at least some conventional catheters, geometrical irregularities (e.g., curves, narrowings, and asymmetries, among other examples) of body lumens may complicate the reliable and consistent formation of desirable treatment profiles. For example, in many neuromodulation treatments, it is desirable to form a helical lesion or pattern of lesions, which may allow substantially all nerves around the circumference of a body lumen to be modulated without forming a potentially problematic fully circumferential lesion in any single transverse plane. Other examples of desirable treatment profiles may be non-helical.

Known types of neuromodulation catheters suitable for forming helical lesions or patterns of lesions include a therapeutic element having a resilient or otherwise expandable structure carrying a plurality of electrodes and may be capable of reliably achieving complete deployment within a cylindrical body lumen. In some cases, however, the desired or target body lumen may not be cylindrical. For example, renal neuromodulation can include modulating nerves at or near treatment locations within renal arteries, which are often relatively short and tortuous. When a therapeutic element of a neuromodulation catheter is deployed at a treatment location within a lumen segment that is non-cylindrical (e.g., not straight and/or having an inconsistent cross-sectional area in successive transverse planes), it may be challenging to reliably attain complete deployment of the therapeutic element and thereby achieve simultaneous, stable, and/or otherwise therapeutically effective contact between electrodes carried by the therapeutic element and an inner surface of a wall of a body lumen.

When a therapeutic element is not completely deployed, energizing an electrode carried by the therapeutic element may form an incomplete lesion, such as a lesion that does not penetrate the wall of the body lumen deeply enough to modulate the sympathetic nerve(s) proximate the electrode. To improve the likelihood of forming a complete lesion, a clinician may reposition the therapeutic element until complete deployment of the therapeutic element is achieved, as may be indicated by adequate impedance measured through the electrode. Alternatively, a clinician may compensate for incomplete deployment by forming multiple lesions at different positions on the body lumen. Each of these options is time consuming and may increase the risk of undesirable complications. Furthermore, incomplete deployment of a therapeutic element may go undetected and diminish the therapeutic effect of a neuromodulation treatment.

Neuromodulation catheters configured in accordance with embodiments of the present technology can at least partially address one or more of the problems described above and/or other problems associated with known neuromodulation technologies whether or not stated herein. For example, a neuromodulation catheter configured in accordance with a particular embodiment includes an elongate shaft and a therapeutic element operably connected to the shaft. The therapeutic element includes an elongate support member and a plurality of radial-expansion members operably connected to the support member. The individual radial-expansion members each carry an electrode and are configured to independently expand radially outward from the support member when the therapeutic elements each transition from a low-profile delivery state to a deployed state at a treatment location within a body lumen. The plurality of radial-expansion members is configured to urge the electrodes into contact with an inner surface of a wall of the lumen segment at a series of longitudinally and circumferentially spaced-apart contact regions. The relative independence of the radial expansion of a given radial-expansion member relative to other radial-expansion members on the catheter and/or other features of the neuromodulation catheter may facilitate reliably achieving complete deployment of the therapeutic element. For example, when the therapeutic element is deployed at a treatment location within a lumen segment that is not straight and/or has an inconsistent cross-sectional area in successive transverse planes, the effect of these anatomical characteristics can be localized.

Specific details of several embodiments of the present technology are described herein with reference to FIGS. 1A-10B. Although many of the embodiments are described herein with respect to devices, systems, and methods for percutaneous intravascular renal neuromodulation, other applications and other embodiments in addition to those described herein are within the scope of the present technology. For example, at least some embodiments may be useful for neuromodulation within a body lumen other than a blood vessel, for extravascular neuromodulation, for non-renal neuromodulation, and/or for use in therapies other than neuromodulation. It should be noted that other embodiments in addition to those disclosed herein are within the scope of the present technology. Furthermore, embodiments of the present technology can have different configurations and components, and may be used for procedures different from those disclosed herein. Moreover, a person of ordinary skill in the art will understand that embodiments of the present technology can have configurations, components, and/or procedures in addition to those disclosed herein and that these and other embodiments can be without several of the configurations, components, and/or procedures disclosed herein without deviating from the present technology.

As used herein, the terms "distal" and "proximal" define a position or direction with respect to a clinician or a clinician's control device (e.g., a handle of a catheter). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

Selected Examples of Neuromodulation Catheters and Related Devices

FIG. 1A is a perspective view of a system 100 (e.g., a neuromodulation system) configured in accordance with an embodiment of the present technology. The system 100 can include a catheter 102 (e.g., a neuromodulation catheter), a console 104, and a cable 106 extending therebetween. The catheter 102 can include an elongate shaft 108 having a proximal end portion 110 and a distal end portion 112. The catheter 102 can further include a handle 114 and a therapeutic element 116 (e.g., a neuromodulation element) operably connected to the shaft 108 via, respectively, the proximal and distal end portions 110, 112 of the shaft 108. The shaft 108 can be configured to locate the therapeutic element 116 intravascularly at a treatment location within a body lumen, such as a suitable blood vessel, duct, airway, or other naturally occurring lumen within the human body. The therapeutic element 116 can be configured to provide or support a treatment (e.g., a neuromodulation treatment) at the treatment location.

Therapeutic element 116 can be configured to be radially constrained and slidably disposed within a delivery sheath (see FIGS. 7A-7D) while the catheter 102 is being deployed within a body lumen. The outside diameter of the sheath can be 2, 3, 4, 5, 6, or 7 French or another suitable size. As an example, deployment of the catheter 102 can include percutaneously inserting a medical guide wire (not shown) into a body lumen of a patient and advancing the catheter 102 along the guide wire until the therapeutic element 116 reaches a suitable treatment location. As another example, the catheter 102 can be steerable or non-steerable and configured for deployment without a guide wire. Catheter 102 can also be configured for deployment via a guide catheter (not shown) with or without the use of a delivery sheath or guide wire.

The console 104 can be configured to control, monitor, supply energy, and/or otherwise support operation of the catheter 102. Alternatively, the catheter 102 can be self-contained or otherwise configured for operation without connection to a console 104. When present, the console 104 can be configured to generate a selected form and/or magnitude of energy for delivery to tissue at or near a treatment location via the therapeutic element 116. The console 104 can have different configurations depending on the treatment modality of the catheter 102. When the catheter 102 is configured for electrode-based, heat-element-based, or transducer-based treatment, for example, the console 104 can include an energy generator (not shown) configured to generate radio frequency (RF) energy (e.g., monopolar and/or bipolar RF energy), pulsed electrical energy, microwave energy, optical energy, ultrasound energy (e.g., intravascularly delivered ultrasound energy, extracorporeally delivered ultrasound energy, and/or high-intensity focused ultrasound energy), direct heat, radiation (e.g., infrared, visible, and/or gamma radiation), and/or another suitable type of energy. Similarly, when the catheter 102 is configured for chemical-based treatment (e.g., drug infusion), the console 104 can include a chemical reservoir (not shown) and can be configured to supply the catheter 102 with one or more chemicals.

In some embodiments, the system 100 includes a control device 118 along the cable 106. The control device 118 can be configured to initiate, terminate, and/or adjust operation of one or more components of the catheter 102 directly and/or via the console 104. In other embodiments, the control device 118 can be absent or can have another suitable location, such as within the handle 114. The console 104 can be configured to execute an automated control algorithm 120 and/or to receive control instructions from an operator. Furthermore, the console 104 can be configured to provide information to an operator before, during, and/or after a treatment procedure via an evaluation/feedback algorithm 122.

Figure 1C:
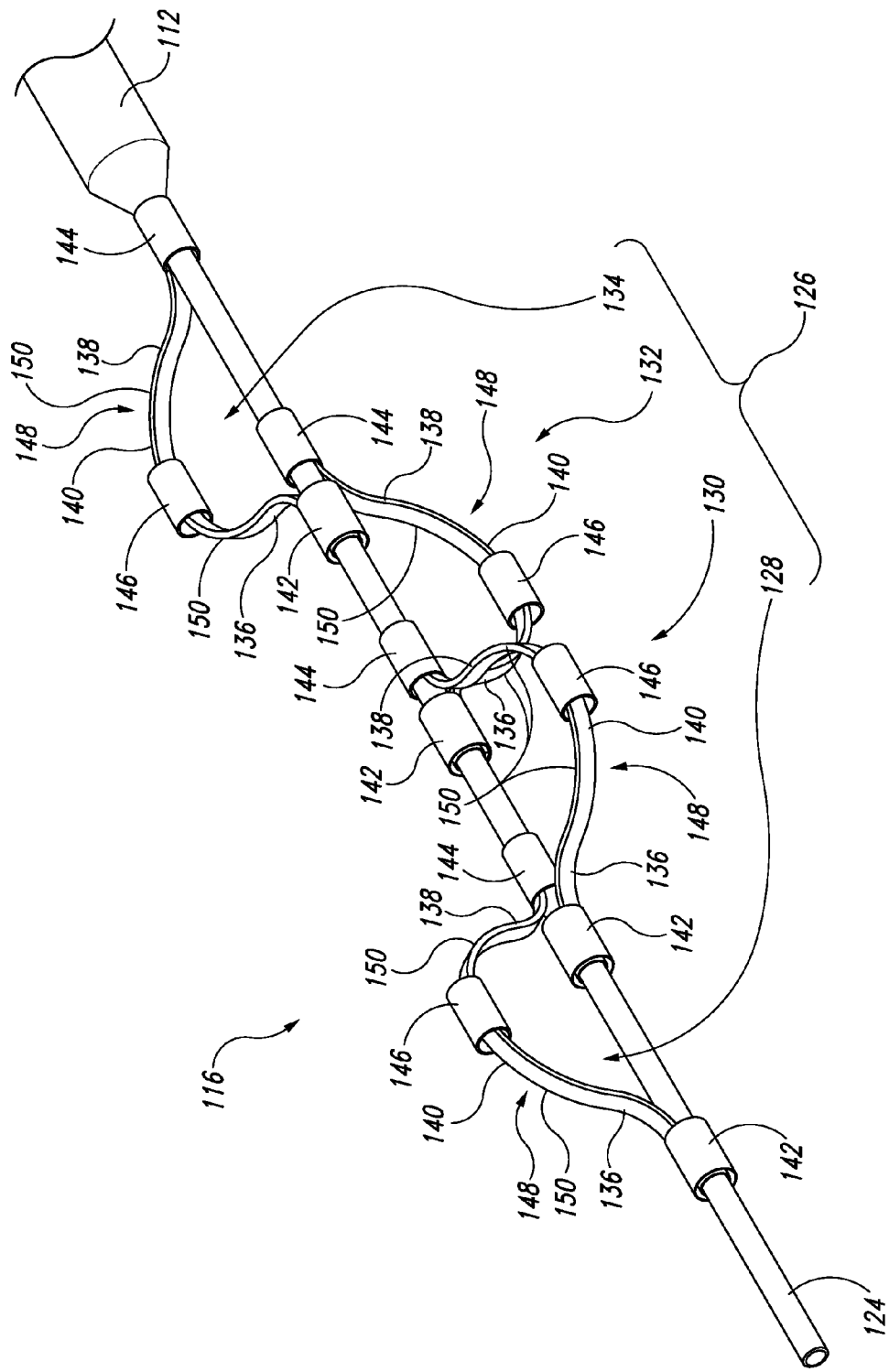

FIGS. 1B and 1C are an enlarged side view and an enlarged perspective view, respectively, of the therapeutic element 116. The therapeutic element 116 can include an elongate support member 124 and a plurality of radial-expansion members 126 operably connected to the support member 124 in a distal-to-proximal sequence. In the illustrated embodiment, the plurality of radial-expansion members 126 includes a first radial-expansion member 128, a second radial-expansion member 130, a third radial-expansion member 132, and a fourth radial-expansion member 134. It will be appreciated, however, that in other embodiments the therapeutic element 116 may include a different number of individual radial-expansion members 126 (e.g., another suitable number less than 10 or a suitable number greater than 10). The individual radial-expansion members 126 can include a distal end portion 136 (e.g., a distal leg) and a proximal end portion 138 (e.g., a proximal leg). One or both of the distal and proximal end portions 136, 138 of the individual radial-expansion members 126 can be moveably (e.g., slidably) connected to the support member 124. Disposed between their respective distal and proximal end portions 136, 138, the individual radial-expansion members 126 can include a bridging portion 140 configured to expand radially outward from the support member 124 in conjunction with the corresponding distal end portion 136 moving proximally toward the corresponding proximal end portion 138 and/or the corresponding proximal end portion 138 moving distally toward the corresponding distal end portion 136.

In the illustrated embodiment, the distal end portions 136 of the individual radial-expansion members 126 include a longitudinally slidable collar 142 mounted about support member 124. The proximal end portions 138 of the individual radial-expansion members 126 include a fixed collar 144 mounted about support member 124. Collars 142, 144 can extend fully or partially around support member 124 or may be replaced with other suitable connecting structures. Also In the illustrated embodiment, individual radial-expansion members each 126 carry an annular electrode 146 at their respective bridging portions 140 and include an electrical lead (not shown) extending along or through their respective proximal end portions 138. In other embodiments, radial-expansion members 126 can include other suitable types and/or positions of electrodes 146 and associated leads. For example, resilient members 126 can be electrically conductive, with bridging portions 140 serving as electrodes and proximal end portions 138 serving as electrical leads. In still other embodiments, individual radial-expansion members 126 can include treatment elements other than electrodes, such as devices suitable for providing other energy-based or chemical-based treatment modalities.

The individual radial-expansion members 126 can be configured to independently expand radially outward from the support member 124 when the therapeutic element 116 transitions from a low-profile delivery state to a deployed state. For example, the individual radial-expansion members 126 can be resiliently biased to move their respective bridging portions 140 radially outward from the support member 124 when each radial-expansion member 126 is released from the inward radial constraint provided by a delivery sheath. Furthermore, the individual radial-expansion members 126 can be configured to self-expand from a radially constrained, stressed condition in the low-profile delivery state to a radially expanded, relaxed condition at a predetermined extent of radial expansion in the deployed state. The plurality of radial-expansion members 126 can be arranged along support member 124 to urge the electrodes 146 into contact with an inner surface of a lumen wall (not shown) at a series of contact regions when the therapeutic element 116 is in the deployed state at a treatment location within a body lumen having the lumen wall. In this way, the therapeutic element 116 can form a desirable treatment profile. For example, the contact regions can be longitudinally and circumferentially spaced apart and, in at least some cases, disposed along a helical path.

Individual radial-expansion members 126 partially overlap longitudinally. For example, the distal and proximal end portions 136, 138 of the plurality of radial-expansion members 126 can be interdigitated and/or the individual radial-expansion members 126 can be longitudinally staggered, nested, and/or interrelated in another suitable manner. This can be useful, for example, to facilitate independent expansion of the individual radial-expansion members 126 without unduly sacrificing longitudinal compactness. The distal end portions 136 of the individual radial-expansion members 126 can be operably connected to the support member 124 at positions between positions at which the distal and proximal end portions 136, 138 of a distally adjacent radial-expansion member 126 (if present) are operably connected to the support member 124. For example, the distal end portions 136 of the individual radial-expansion members 126 can be fixedly connected to or longitudinally slidable along segments of the support member 124 between distal and proximal end portions 136, 138 of a distally adjacent radial-expansion member 126 (if present). Similarly, the proximal end portions 138 of the individual radial-expansion members 126 can be operably connected to the support member 124 at positions between positions at which the distal and proximal end portions 136, 138 of the proximally adjacent radial-expansion member 126 (if present) are operably connected to the support member 124. For example, the proximal end portions 138 of the individual radial-expansion members 126 can be fixedly connected to or longitudinally slidable along segments of the support member 124 between distal and proximal end portions 136, 138 of a proximally adjacent radial-expansion member 126 (if present).

In the illustrated embodiment, the individual radial-expansion members 126 include a bow-shaped ribbon 148 made of metal (e.g., spring tempered stainless steel or titanium nickel alloy commonly known as nitinol) and having sigmoid, i.e. C-shaped, or bell-shaped portions 150 with opposite orientations at opposite sides of the bridging portion 140. In other embodiments, the radial-expansion members 126 can have other forms suitable for radial expansion to place bridging portions 140 in apposition with the inner wall of a body lumen. For example, the individual radial-expansion members 126 can include a wire (not shown) in place of the ribbon 148. As another example, the individual radial-expansion members 126 can each include a tubular structure (not shown) in place of the ribbon 148, such as to facilitate routing electrical leads from the support member 124 to the electrodes 146. As yet another example, the individual radial-expansion members 126 can include resiliency-enhancing structural features (not shown), such as compact helical or sinusoidal bends along all or a portion of the length of the ribbon 148. As yet another example, the overall shape of the individual radial-expansion members 126 can be angular rather than curved. Other suitable variations in the characteristics of the individual radial-expansion members 126 are also possible.

Figure 2A:
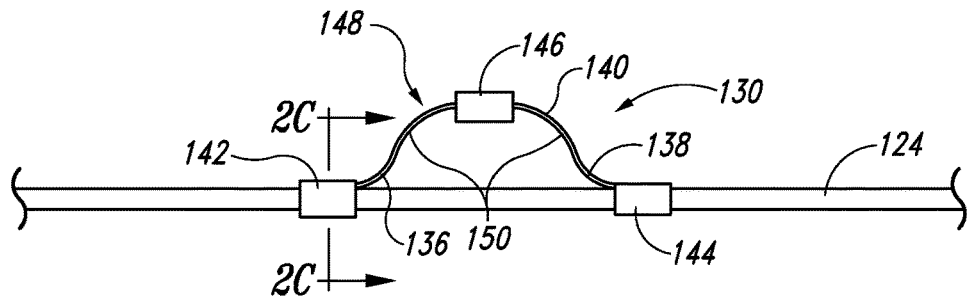
FIGS. 2A and 2B are side views of a radial-expansion member and an associated segment of a support member of the therapeutic element shown in FIGS. 1A-1C.
Figure 2B:
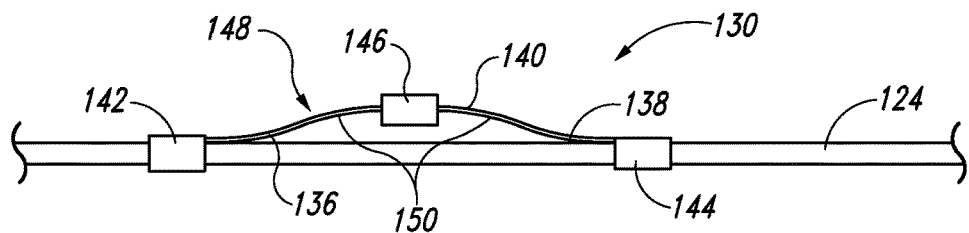

FIGS. 2A and 2B are side views of the second radial-expansion member 130 and an associated segment of the support member 124 with the other radial-expansion members 126 omitted for clarity of illustration. In FIG. 2A, the second radial-expansion member 130 is shown in a radially extended state. In FIG. 2B, the second radial-expansion member 130 is shown in a radially constrained state. As illustrated in FIGS. 2A and 2B, the second radial-expansion member 130 can be configured to move between the extended and constrained states by longitudinal movement of the distal end portion 136 along support member 124 while the proximal end portion 138 remains fixed to support member 124. This can be useful, for example, to facilitate smooth transitioning of the therapeutic element 116 from the deployed state to the low-profile delivery state as the therapeutic element 116 is retracted into a sheath (not shown), such as by reducing or eliminating catching of the radial-expansion members 126 on a distal lip of the sheath.

Figure 2C:
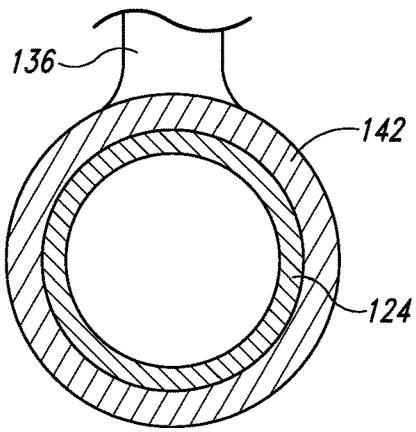
FIG. 2C is an enlarged cross-sectional view of the therapeutic element shown in FIG. 1A taken along the line 2C-2C in FIG. 2A.
Figure 2D:
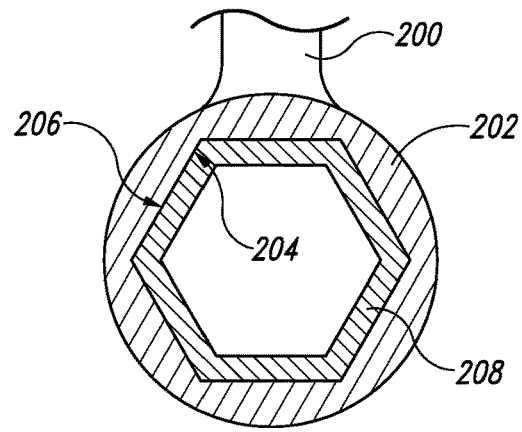
FIGS. 2D and 2E are enlarged cross-sectional views of therapeutic elements of catheters configured in accordance with additional embodiments of the present technology taken along transverse planes similar to the plane corresponding to the line 2C-2C in FIG. 2A.
Figure 2E:
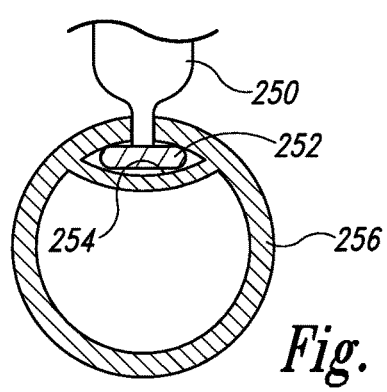

FIG. 2C is an enlarged cross-sectional view of the therapeutic element 116 taken along the line 2C-2C in FIG. 2A. As illustrated in FIG. 2C, the slidable collar 142 can be configured to slide along an exterior surface of a segment of the support member 124. FIGS. 2D and 2E are enlarged cross-sectional views of therapeutic elements of catheters configured in accordance with additional embodiments of the present technology taken along transverse planes similar to the plane corresponding to the line 2C-2C in FIG. 2A. As shown in FIG. 2D, in some embodiments, a distal end portion 200 of a radial-expansion member (not separately identified in FIG. 2D) includes a slidable collar 202 that has a non-circular inner surface in a transverse plane. The slidable collar 202 and a corresponding outer surface 206 of a support member 208 can be keyed. As shown in FIG. 2E, in other embodiments, a distal end portion 250 of a radial-expansion member (not separately identified in FIG. 2E) includes an enlarged head 252 slidably disposed within a channel 254 defined by a support member 256. The channel 254 can be a common channel that receives heads 252 of distal end portions 250 of multiple radial-expansion members (not shown) or a discrete channel that receives only the head 252 shown in FIG. 2E. In the latter case, the channel 254 can be one of a plurality of channels that individually receive different heads 252.

Features of the embodiments shown in FIGS. 2D and 2E may restrict circumferential, e.g. rotational movement of the slidable collars 142, 202 relative to respective support members 208, 256. This can be useful, for example, when it is desirable to maintain precise radial orientations s of the distal end portions 200, 250, respectively. As another potential advantage, features of the embodiments shown in FIGS. 2D and 2E that restrict rotational movement of the distal end portions 200, 250 relative to the respective support members 208, 256 may reduce or prevent twisting of leads. Leads and other features (e.g., guide-wire lumens and structural members, among others) within the support members 124, 208, 256 are omitted in FIGS. 2C-2E for simplicity of illustration.

Figure 3A:
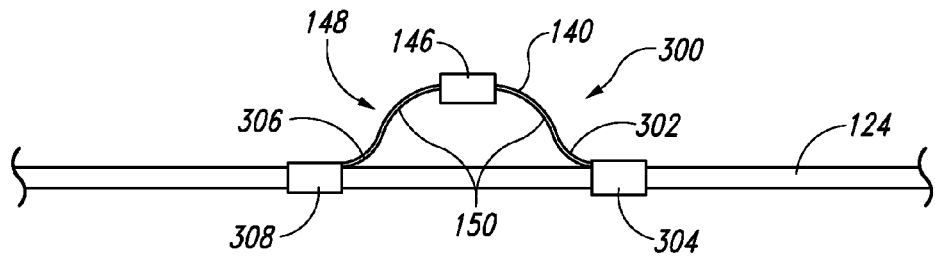
FIGS. 3A and 3B are side views of a radial-expansion member and an associated segment of a support member of a therapeutic element of a catheter configured in accordance with another embodiment of the present technology.
Figure 3B:
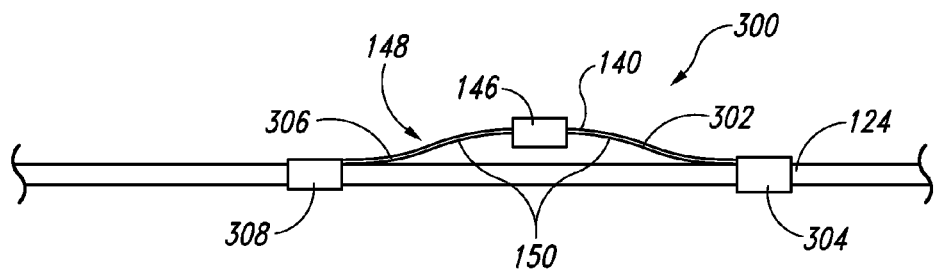
Figure 4A:
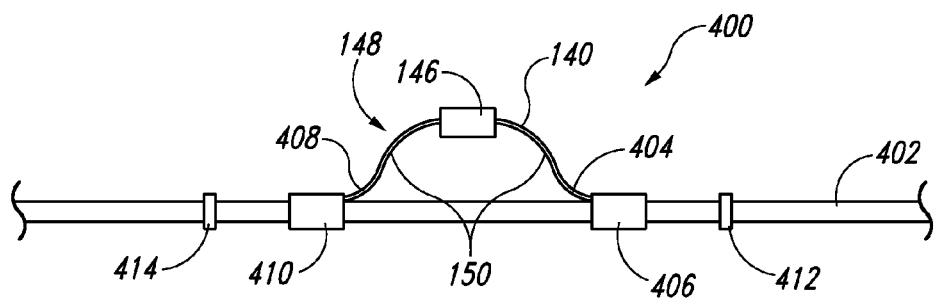
FIGS. 4A and 4B are side views of a radial-expansion member and an associated segment of a support member of a therapeutic element of a catheter configured in accordance with another embodiment of the present technology.
Figure 4B:
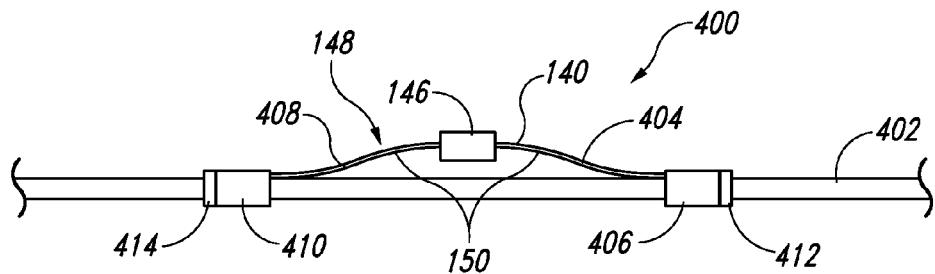

FIGS. 3A-4B illustrate movement of radial-expansion members relative to corresponding support members in catheters configured in accordance with additional embodiments of the present technology. As one example, FIGS. 3A and 3B are side views of a radial-expansion member 300 and an associated segment of the support member 124 with the radial-expansion member 300 shown in a radially extended state in FIG. 3A and in a radially constrained state in FIG. 3B. Unlike the radial-expansion members 126, the radial-expansion member 300 includes a proximal end portion 302 having a longitudinally slidable collar 304 and a distal end portion 306 having a fixed collar 308. As another example, FIGS. 4A and 4B are side views of a radial-expansion member 400 and an associated segment of a support member 402 with the radial-expansion member 400 shown in a radially extended state in FIG. 4A and in a radially constrained state in FIG. 4B. Unlike the radial-expansion members 126, 300, the radial-expansion member 400 includes a proximal end portion 404 having a longitudinally slidable collar 406 and a distal end portion 408 having a longitudinally slidable collar 410. The radial-expansion member 400 can further include a proximal stop 412 and a distal stop 414 fixedly connected to the support member 402 proximal and distal, respectively, to the radial-expansion member 400. The proximal stop 412 can be positioned to restrict proximal movement of the proximal end portion 404. Similarly, the distal stop 414 can be positioned to restrict distal movement of the distal end portion 408. Other arrangements of stops (not shown) can be envisioned in radial-expansion member 400, such as one long stop or two short stops positioned between collars 410, 412 to limit the range of positions that radial-expansion member 400 may take along support member 402 while still permitting the radially extended state shown in FIG. 4A to be fully attained.

With reference to again FIGS. 1A-1C, in the illustrated embodiment, the individual radial-expansion members 126 are circumferentially offset and longitudinally staggered relative to one another. This arrangement can be such that the therapeutic element 116 has an asymmetrical cross section in each transverse plane intersecting a given bridging portion 140. The incremental circumferential offset, i.e. the angular offset about support member 124, from a given radial-expansion member 126 to a proximally successive radial-expansion member 126 can be 90 degrees. For example, looking proximally from a distal end of the support member 124, the first radial-expansion member 128 can be oriented at 12 o'clock (0 degrees), the second radial-expansion member 130 can be oriented at 3 o'clock (90 degrees), the third radial-expansion member 132 can be oriented at 6 o'clock (180 degrees), and the fourth radial-expansion member 134 can be oriented at 9 o'clock (270 degrees). In other embodiments, the circumferential offset can be greater than 90 degrees (e.g., within a range from 90 degrees to 180 degrees) or less than 90 degrees (e.g., within a range from 5 degrees to 90 degrees).

Figure 5:
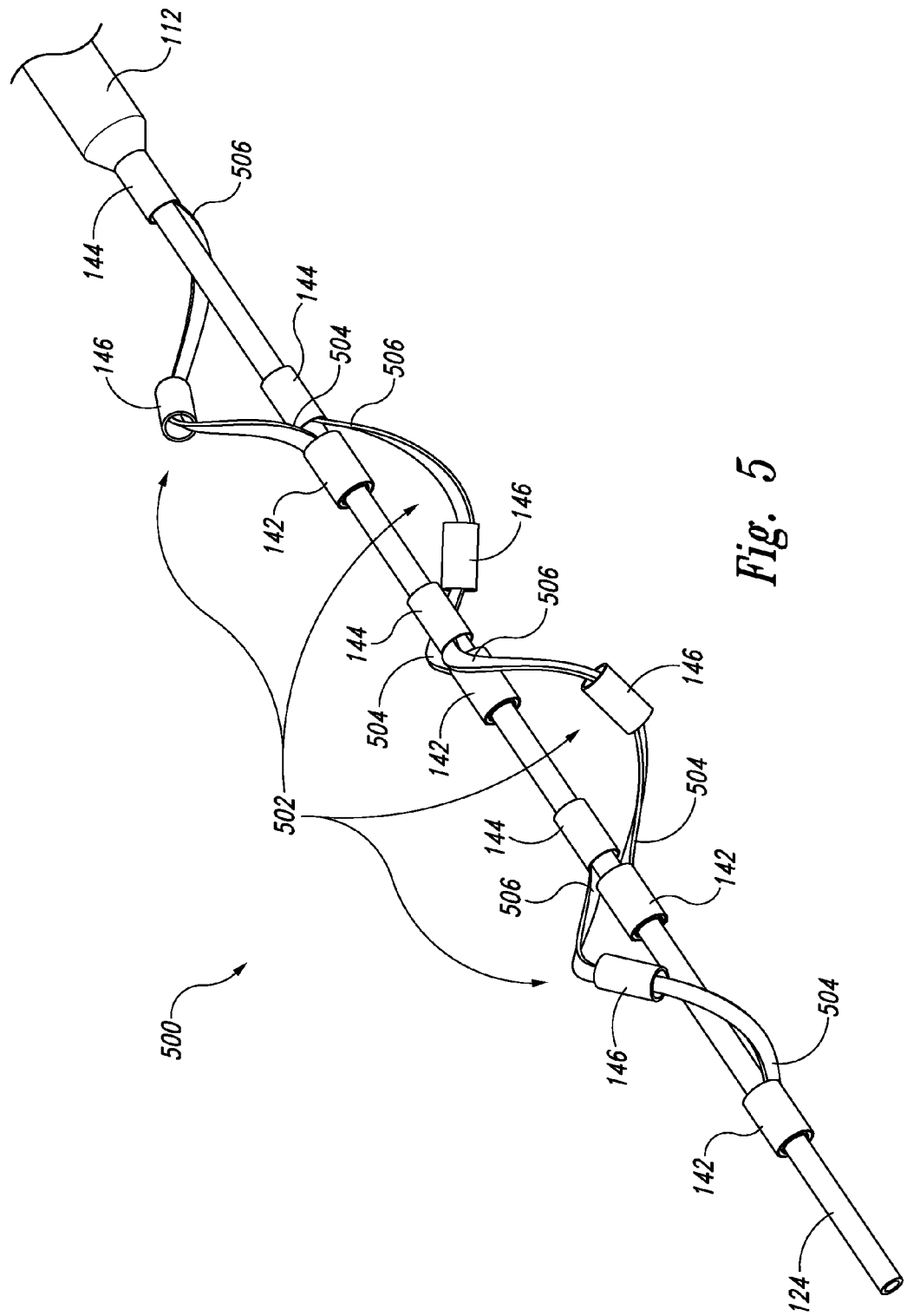
FIGS. 5 and 6 are perspective views of therapeutic elements of catheters configured in accordance with additional embodiments of the present technology.
Figure 6:
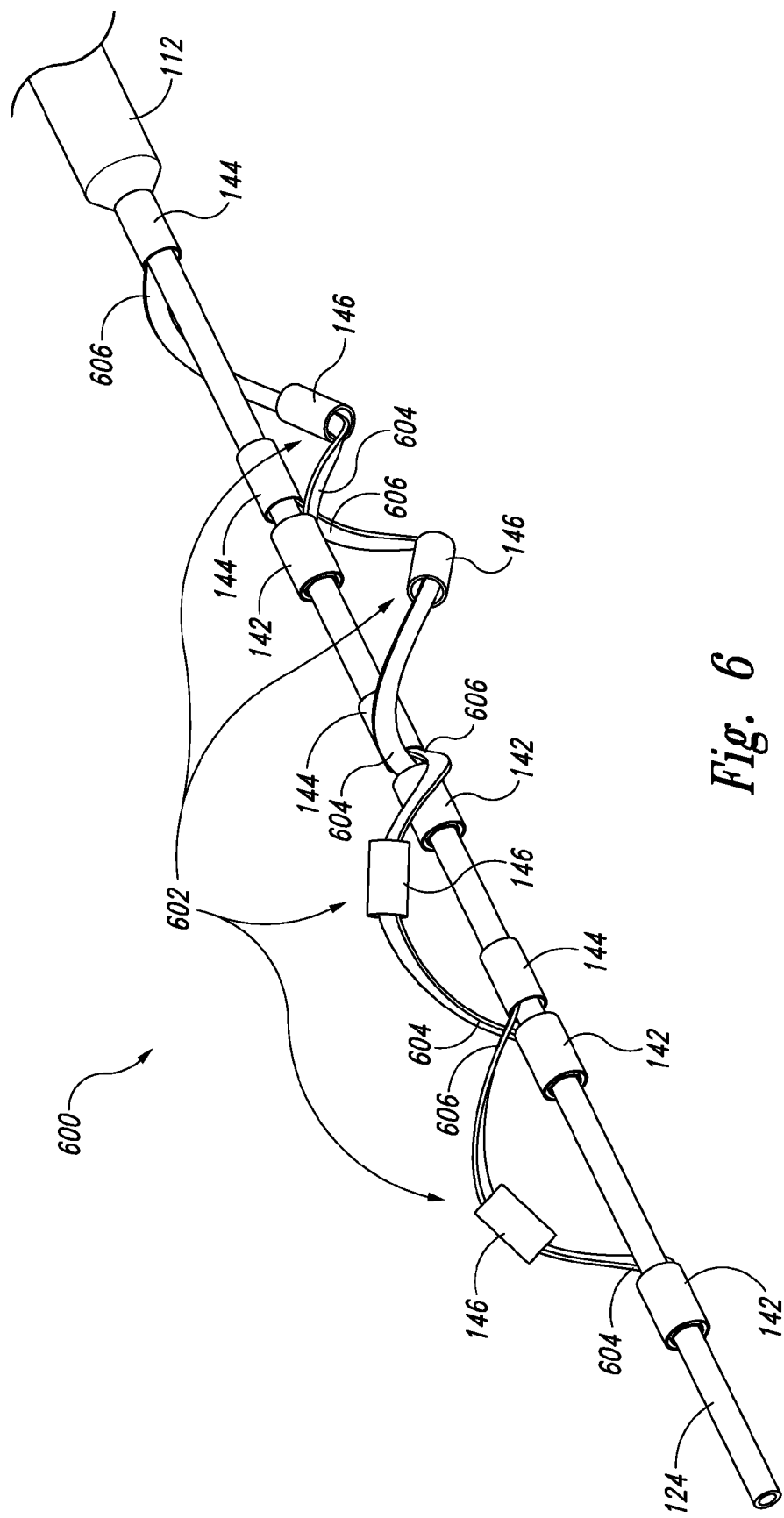

In some embodiments, the individual radial-expansion members 126 are planar with the distal and proximal end portions 136, 138 of a given radial-expansion member 126 having the same radial orientation relative to the support member 124. In other embodiments, the individual radial-expansion members 126 can be non-planar and the distal and proximal end portions 136, 138 of a given radial-expansion member 126 can have different radial orientations relative to the support member 124. FIGS. 5 and 6, for example, illustrate examples of non-planar radial-expansion members of therapeutic elements of catheters configured in accordance with additional embodiments of the present technology. FIG. 5 is a perspective view of a therapeutic element 500 including a plurality of non-planar radial-expansion members 502 that are twisted such that distal and proximal end portions 504, 506 of a given radial-expansion member 502 are circumferentially offset from one another. This can be useful, for example, to enhance alignment of the electrodes 146 with a desirable treatment profile, such as a helical treatment profile.

Similar to the therapeutic element 116 shown in FIG. 1A, in the embodiment shown in FIG. 5, the radial-expansion members 502 are circumferentially fully offset from one another. In contrast, FIG. 6 is a perspective view of a therapeutic element 600 including non-planar radial-expansion members 602 that are circumferentially interwoven. The radial-expansion members 602 can extend away from the support member 124 along one side of distally neighboring radial-expansion member 602 and twist back toward the support member along an opposite side of a proximally neighboring radial-expansion member 602. In other words, the distal end portion 604 of a given radial-expansion member 602 can be circumferentially offset to one side of a proximal end portion 606 of a distally neighboring radial-expansion member 602 while the proximal end portion 606 of the given radial-expansion member 602 is circumferentially offset to the opposite side of a distal end portion 604$_{[KM1]}$ of a proximally neighboring radial-expansion member 602. This can be useful, to further enhance alignment of the electrodes 146 with a desirable treatment profile, such as a helical treatment profile. For example, circumferentially interweaving the radial-expansion members 602 may reduce or prevent interference between neighboring radial-expansion member 602 during expansion and contraction even when the radial-expansion members 602 are sharply twisted. In other embodiments, radial-expansion members can have other suitable configurations.

Figure 7A:
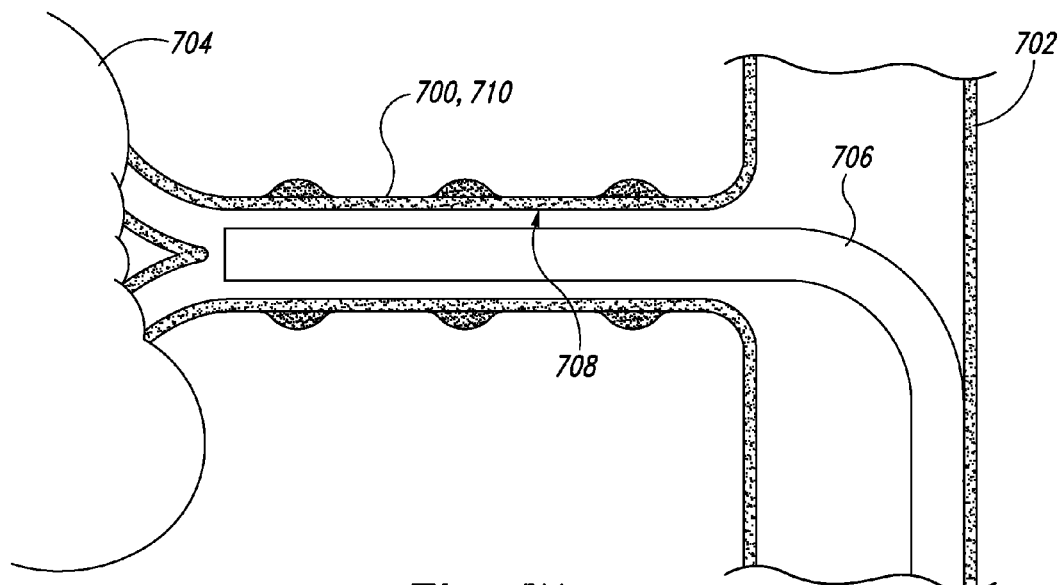
FIGS. 7A-7D are enlarged anatomical side views of the therapeutic element shown in FIG. 1A and associated components located at a treatment location within a renal artery.

FIGS. 7A-7D are enlarged anatomical side views of the therapeutic element 116 shown in FIG. 1A and associated components being used for renal neuromodulation at a treatment site within a renal artery 700 that extends between an aorta 702 and a kidney 704 in a human patient. The therapeutic element 116 can also be used for other purposes and at treatment locations within other suitable body lumens. To locate the therapeutic element 116 at the treatment location, the catheter 102 can be advanced toward the treatment location while the therapeutic element 116 is radially constrained in a low-profile delivery state within a delivery sheath 706. In FIG. 7A, the therapeutic element 116 is in the delivery state hidden within the sheath 706. It will be understood by persons familiar with the field of catheterization that catheter 102 and sheath 706 would typically be guided, simultaneously or separately, from a vascular puncture site to renal artery 700 using a guiding catheter and/or a medical guidewire, both of which are omitted from FIGS. 7A-7D for simplicity of illustration.

Figure 7B:
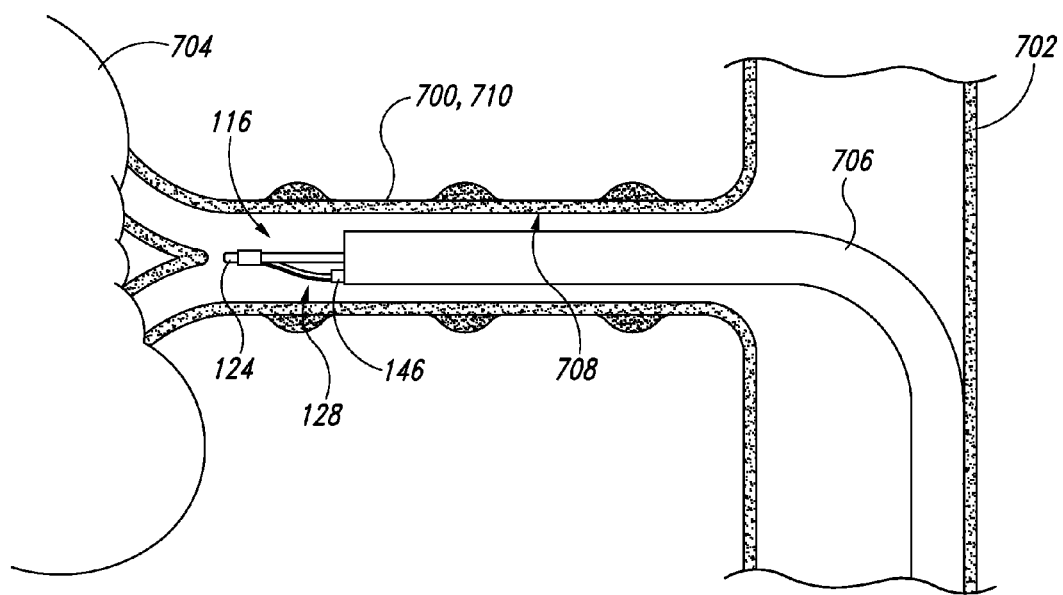
Figure 7C:
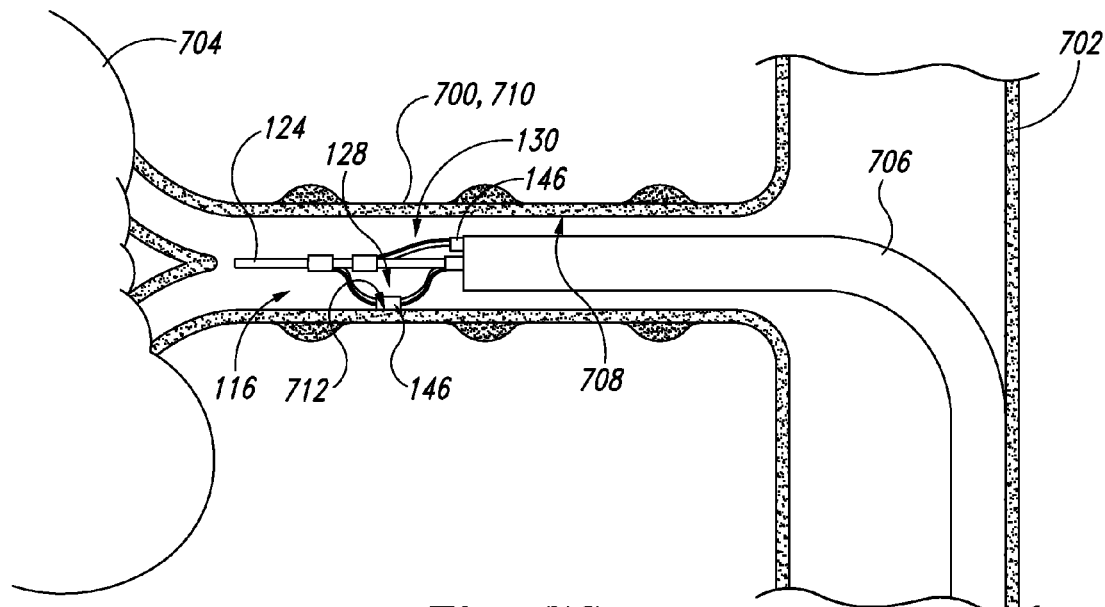
Figure 7D:
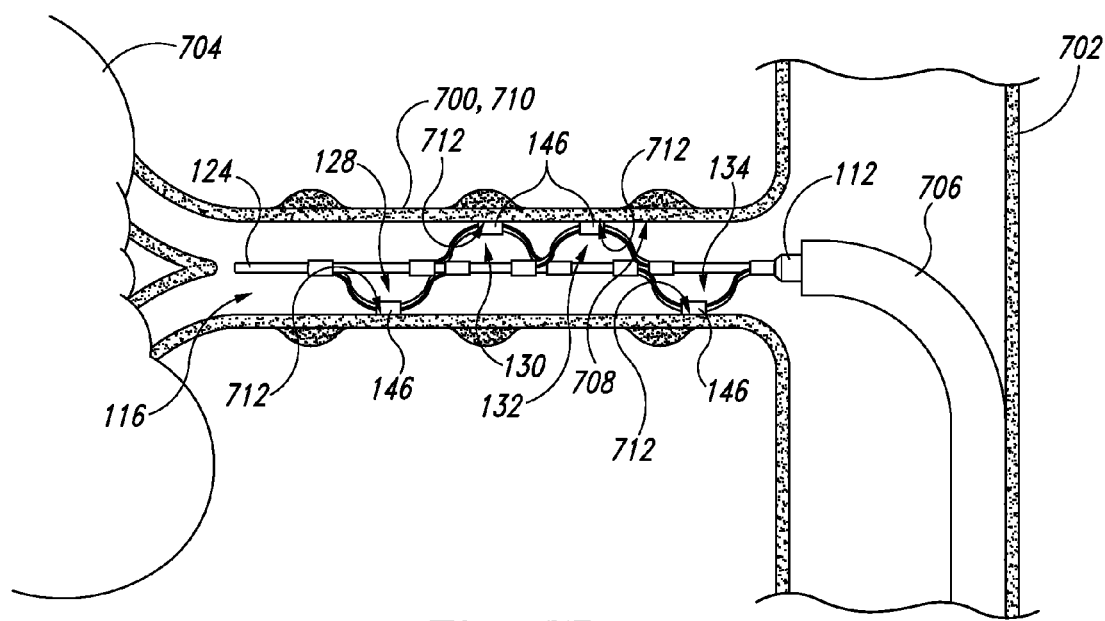

In FIG. 7B, the therapeutic element 116 is shown in a first intermediate state as it transitions from the delivery state to a deployed state. Sheath 706 is shown as having been withdrawn from renal artery 700 sufficiently to expose only a distal portion of first radial expansion member 128, which remains radially constrained by delivery sheath 706. In FIG. 7C, the therapeutic element 116 is shown in a second intermediate state as it transitions from the first intermediate state to the deployed state. Sheath 706 is shown as having been withdrawn from renal artery 700 sufficiently to expose all of first radial expansion member 128, which has self-expanded into apposition with inner surface 708 of a wall 710 of the renal artery 700. As shown in FIGS. 7B and 7C, deploying the therapeutic element 116 can include independently expanding the radial-expansion members 128, 130, 132, 134 one at a time in a distal-to-proximal sequence. This can include retracting the sheath 706 relative to the catheter 102 (FIG. 1A) and/or advancing the catheter 102 relative to the sheath 706 so as to allow the unconstrained radial-expansion members 126 to resiliently urge the electrodes 146 toward an inner surface 708 of a wall 710 of the renal artery 700. In FIG. 7D, the therapeutic element 116 is shown in the deployed state. Sheath 706 is shown as having been withdrawn from renal artery 700 sufficiently to expose all radial expansion members 128, 130, 132, 134, which have self-expanded into apposition with inner surface 708 of a wall 710 of the renal artery 700. In the embodiment shown, radial expansion members 128, 130, 132, 134 are configured such that electrodes 146 form a series of longitudinally and circumferentially spaced-apart contact regions 712 disposed along a helical path. After therapeutic element 116 is deployed at the treatment location, electrodes 146 can be energized to modulate one or more nerves at or near the treatment location.

Figure 8:
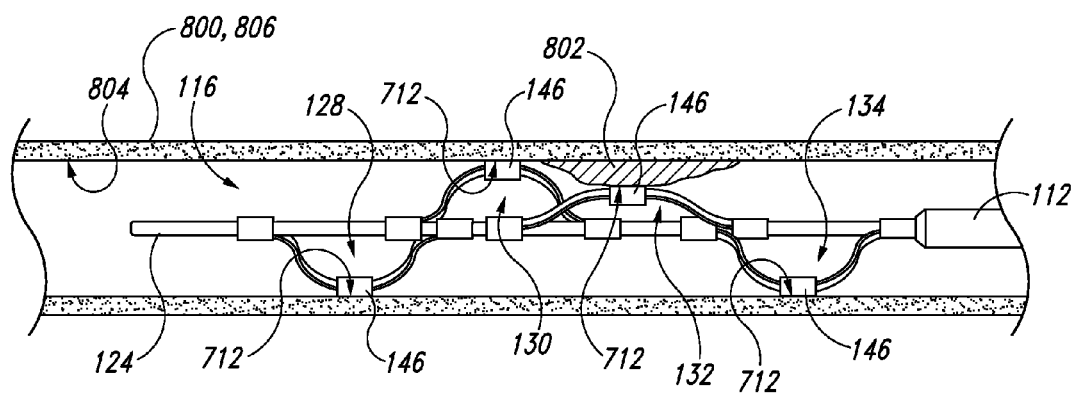
FIG. 8 is an enlarged anatomical side view of the therapeutic element shown in FIG. 1A in a deployed state and located at a treatment location within a lumen segment including an obstruction.

As discussed above, catheters configured in accordance with at least some embodiments of the present technology are expected to treat tissue (e.g., nerves) at or near treatment locations within geometrically irregular (e.g., non-cylindrical) segments of body lumens in a reliable and consistent manner. For example, FIG. 8 is an enlarged anatomical side view of the therapeutic element 116 in the deployed state and located at a treatment location within a lumen segment 800 including an obstruction 802. As shown in FIG. 8, the obstruction 802 is expected to partially inhibit full radial expansion of some, but not all, of the radial-expansion members 126, such as the third radial-expansion member 132 only. This, however, is expected to have little or no effect on radial expansion of the other radial-expansion members 126 or on the ability of the therapeutic element 116 to achieve stable contact between the electrodes 146 and an inner surface 804 of a wall 806 of the lumen segment 800.

Figure 9:
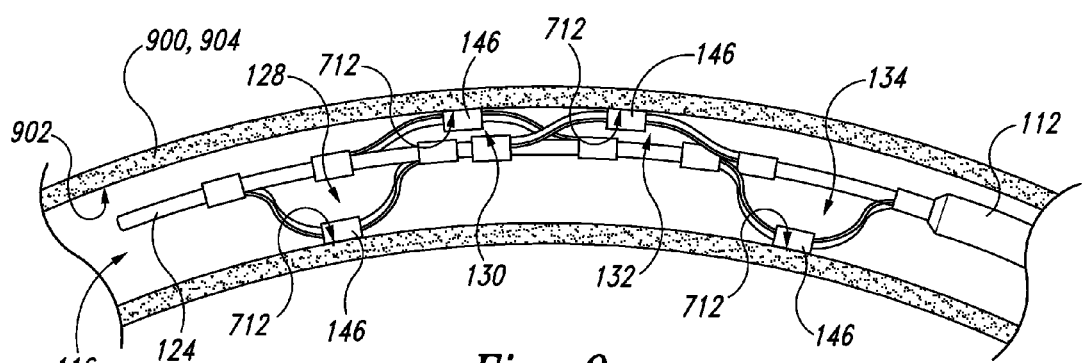
FIG. 9 is an enlarged anatomical side view of the therapeutic element shown in FIG. 1A in a deployed state and located at a treatment location within a non-uniform lumen segment.

As another example, FIG. 9 is an enlarged anatomical side view of the therapeutic element 116 in the deployed state and located at a treatment location within a curved lumen segment 900. As shown in FIG. 9, the curve is expected to urge the support member 124 away from the center of the lumen segment 900 and thereby partially inhibit full radial expansion of some, but not all, of the radial-expansion members 126, such as the second and third radial-expansion members 130, 132 only. This, however, is expected to have little or no effect on the radial expansion of the other radial-expansion members 126 or on the ability of the therapeutic element 116 to achieve stable contact between the electrodes 146 and an inner surface 902 of a wall 904 of the lumen segment 900. The behavior illustrated in FIGS. 8 and 9 is by way of theory only and is not intended to limit the scope of the present technology. The therapeutic element 116 may behave differently in practice and may have the same or different advantages. Furthermore, the therapeutic element 116 may have advantages entirely distinct from the advantages described with reference to FIGS. 8 and 9.

As discussed above with reference to FIGS. 7A-7D, in some embodiments, radial-expansion members are configured to expand one at a time in a distal-to-proximal sequence. In other embodiments, radial-expansion members can be configured to expand in another suitable manner, such as simultaneously. FIGS. 10A-10B illustrate three radial-expansion members 1000 (individually identified as radial-expansion members 1000*a-c*) configured to be exposed from within a sheath (not shown) and then expanded (e.g., simultaneously expanded) by retraction of a control member 1002. The radial-expansion members 1000 can be operably connected to a support element 1003 including a tube 1004 defining a lumen 1006. For clarity of illustration, only distal portions of the respective radial-expansion members 1000 are shown in FIGS. 10A-10B. At their respective distal portions, the radial-expansion members 1000 can include a neck 1008. The tube 1004 can include a series of slots 1010 through which the individual necks 1008 respectively extend. The individual radial-expansion members 1000 can further include a nub 1012 connected to a distal end of the neck 1008. Proximal end portions (not shown) of the radial-expansion members 1000 can be fixedly connected to the tube 1004. The individual radial-expansion members 1000 can have different circumferential positions about a longitudinal axis of the support element 1003. In FIGS. 10A-10B, however, the individual radial-expansion members 1000 are shown in the same plane for clarity of illustration.

The control member 1002 can be slidably received within the lumen 1006. In the illustrated embodiment, the control member 1002 includes a series of stepped-down segments 1014 (individually identified as stepped-down segments 1014*a-d*) arranged from proximal to distal with successively decreasing diameters. The control member 1002 can further include shoulders or beveled ledges 1016 individually positioned between longitudinally neighboring pairs of the stepped-down segments 1014. A guide-wire lumen (not shown) can extend longitudinally through a central region of the control member 1002, such as in alignment with the distalmost stepped-down segment 1014*d*. In at least some other embodiments, the control member 1002 has a more consistent diameter, such as a diameter equal to the diameter of the distalmost stepped-down segment 1014*d*. In these embodiments, for example, the control member 1002 can include longitudinally spaced apart rings or other circumferential enlargements (not shown) arranged from proximal to distal with successively increasing diameters. This can be useful, for example, to increase the flexibility of the control member 1002.

In FIGS. 10A and 10B, the radial-expansion members 1000 are shown in radially constrained states and radially expanded states, respectively. During delivery to a treatment location, the control member 1002 can hold the radial-expansion members 1000 in the radially constrained states. For example, the control member 1002 can be at a distally advanced position with the beveled ledges 1016 respectively pressing against the nubs 1012 to hold the radial-expansion members 1000 in the radially constrained states. The radial-expansion members 1000 can be resiliently biased toward the radially expanded states. To expand the radial-expansion members 1000, the control member 1002 can be refracted proximally to release constraint on the radial-expansion members 1000 and thereby allow the radial-expansion members 1000 to assume the radially constrained states.

The distal necks 1008, the nubs 1012, or both, can be configured to interact with (e.g., to catch) different respective beveled ledges 1016. This can facilitate independent expansion of the radial-expansion members 1000. For example, the distal necks 1008 can have successively increasing lengths from proximal to distal so as to align the nubs 1012 with respective beveled ledges 1016. Alternatively or in addition, the nubs 1012 can have successively increasing sizes from proximal to distal so as to catch different respective beveled ledges 1016. As the control member 1002 is refracted proximally, any stepped-down segments 1014 distal to a given beveled ledge 1016 aligned with a given nub 1012 can pass by the given nub 1012 without restricting the corresponding radial-expansion member 1000 from moving into its radially constrained state, such as due to the presence of an obstruction or a curve in a lumen segment within which the radial-expansion member 1000 is positioned. This can facilitate the independent operation of the radial-expansion member 1000.

Renal Neuromodulation

Catheters configured in accordance with at least some embodiments of the present technology can be well suited (e.g., with respect to sizing, flexibility, operational characteristics, and/or other attributes) for performing renal neuromodulation in human patients. Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment locations during a treatment procedure. The treatment location can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery. Various suitable modifications can be made to the catheters described above to accommodate different treatment modalities. For example, the electrodes 146 (FIG. 1B) can be replaced with transducers to facilitate transducer-based treatment modalities. As another example, the electrodes 146 can be replaced with drug-delivery elements (e.g., needles) to facilitate chemical-based treatment modalities. Other suitable modifications are also possible.

Renal neuromodulation can include an electrode-based or treatment modality alone or in combination with another treatment modality. Electrode-based or transducer-based treatment can include delivering electricity and/or another form of energy to tissue at or near a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at or near a treatment location. For example, neuromodulation in accordance with embodiments of the present technology can include delivering RF energy, pulsed electrical energy, microwave energy, optical energy, focused ultrasound energy (e.g., high-intensity focused ultrasound energy), and/or another suitable type of energy. An electrode or transducer used to deliver this energy can be used alone or with other electrodes or transducers in a multi-electrode or multi-transducer array.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array, which can be curved or straight.

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of luminal structures that perfuse the target neural fibers. In cases where luminal structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of luminal structures that perfuse the target fibers. In some patients, it can be desirable to heat tissue to temperatures that are sufficient to ablate the target neural fibers or the luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at or near a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at or near a treatment location. For example, chemicals can be delivered via one or more needles originating outside the body or within the vasculature or other body lumens. In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at or near a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

The methods disclosed herein include and encompass, in addition to methods of practicing the present technology (e.g., methods of making and using the disclosed devices and systems), methods of instructing others to practice the present technology. For example, a method in accordance with a particular embodiment includes advancing an elongate shaft of a neuromodulation catheter toward a treatment location within a body lumen of a human patient while a neuromodulation element of the catheter is in a low-profile delivery state, independently expanding a series of bow springs of the neuromodulation element one at a time in a distal-to-proximal sequence as the neuromodulation element transitions from the delivery state to a deployed state at the treatment location, and energizing electrodes and/or transducers carried by the bow springs to modulate one or more nerves of the patient while the neuromodulation element is at the treatment location and in the deployed state. A method in accordance with another embodiment includes instructing such a method.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments of the present technology.

I claim:

1. A neuromodulation catheter, comprising:
   an elongate shaft; and
   a neuromodulation element operably connected to the shaft, the neuromodulation element including—
   an elongate support member, and
   a plurality of bow springs operably connected to the support member, the individual bow springs including a distal leg and a proximal leg, the distal and proximal legs of the plurality of bow springs being longitudinally interdigitated,
   wherein the individual bow springs are configured to independently expand radially outward from the support member when the neuromodulation element transitions from a low-profile delivery state to a deployed state.

2. The neuromodulation catheter of claim 1 wherein the distal and proximal legs of the individual bow springs have the same radial orientation relative to the support member.

3. The neuromodulation catheter of claim 1 wherein the distal and proximal legs of the individual bow springs have different radial orientations relative to the support member.

4. The neuromodulation catheter of claim 3 wherein the plurality of bow springs is circumferentially interwoven.

5. The neuromodulation catheter of claim 1 wherein the individual bow springs are self-expanding.

6. The neuromodulation catheter of claim 1 wherein:
   the shaft is configured to locate the neuromodulation element at a treatment location within a body lumen having a lumen wall,
   the individual bow springs carry or otherwise include an electrode and/or a transducer between their respective distal and proximal legs, and
   the plurality of bow springs is configured to urge the electrodes and/or the transducers into contact with an inner surface of the lumen wall at a series of longitudinally and circumferentially spaced-apart contact regions when the neuromodulation element is in the deployed state at the treatment location.

7. The neuromodulation catheter of claim 6 wherein the contact regions are disposed along a helical path.

8. The neuromodulation catheter of claim 1 wherein:
   the plurality of bow springs includes a first bow spring, a second bow spring, and a third bow spring, respectively positioned in a distal-to-proximal sequence;
   the distal leg of the second bow spring is longitudinally slidable along a segment of the support member between the distal and proximal legs of the first bow spring; and the distal leg of the third bow spring is longitudinally slidable along a segment of the support member between the distal and proximal legs of the second bow spring.

9. The neuromodulation catheter of claim 8 wherein:
the proximal leg of the first bow spring is longitudinally slidable along a segment of the support member between the distal and proximal legs of the second bow spring; and
the proximal leg of the second bow spring is longitudinally slidable along a segment of the support member between the distal and proximal legs of the third bow spring.

10. The neuromodulation catheter of claim 8 wherein:
the proximal leg of the first bow spring is fixedly connected to the support member between the distal and proximal legs of the second bow spring; and
the proximal leg of the second bow spring is fixedly connected to the support member between the distal and proximal legs of the third bow spring.

11. The neuromodulation catheter of claim 8 wherein the distal legs of the second and third bow springs individually include a fully or partially circumferential collar configured to slide along an exterior surface of the respective segment of the support member.

12. The neuromodulation catheter of claim 11 wherein the collars and the corresponding exterior surfaces of the support member are keyed to restrict rotation of the collars relative to the support member.

13. The neuromodulation catheter of claim 8 wherein the distal legs of the second and third bow springs individually include an enlarged head slidably disposed within a single channel or, respectively, within different channels defined by the support member.

14. A neuromodulation catheter comprising:
an elongate shaft; and
a neuromodulation element operably connected to the shaft, the neuromodulation element including—
an elongate support member,
a first radial-expansion member having—
a first distal end portion operably connected to the support member at a first position along a length of the support member,
a first proximal end portion operably connected to the support member at a second position along the length of the support member, and
a first bridging portion extending between the first distal end portion and the first proximal end portion, the first bridging portion carrying or otherwise including a first electrode or transducer,
wherein the first bridging portion is configured to expand radially outward from the support member in conjunction with the first distal end portion moving proximally toward the first proximal end portion and/or the first proximal end portion moving distally toward the first distal end portion, and
a second radial-expansion member having—
a second distal end portion operably connected to the support member at a third position along the length of the support member, the third position being between the first and second positions,
a second proximal end portion operably connected to the support member at a fourth position along the length of the support member, the fourth position being proximal to the second position, and
a second bridging portion extending between the second distal end portion and the second proximal end portion, the second bridging portion carrying or otherwise including a second electrode or transducer,
wherein the second bridging portion is configured to expand radially outward from the support member in conjunction with the second distal end portion moving proximally toward the second proximal end portion and/or the second proximal end portion moving distally toward the second distal end portion,
wherein the first radial-expansion member and the second radial-expansion member are configured to expand radially outward from the support member independently of each other.

15. The neuromodulation catheter of claim 14 wherein the first and second radial-expansion members are resiliently biased to expand the first and second bridging portions, respectively, radially outward from the support member.

16. The neuromodulation catheter of claim 14 wherein the neuromodulation element has an asymmetrical cross section in all transverse planes intersecting the second bridging portion.

17. The neuromodulation catheter of claim 14 wherein the second radial-expansion member is slidably connected to the support member via the second distal end portion and fixedly connected to the support member via the second proximal end portion.

18. The neuromodulation catheter of claim 14 wherein the second radial-expansion member is slidably connected to the support member via the second proximal end portion and fixedly connected to the support member via the second distal end portion.

19. The neuromodulation catheter of claim 14 wherein the second radial-expansion member is slidably connected to the support member via the second proximal end portion and via the second distal end portion.

20. The neuromodulation catheter of claim 19 wherein the support member includes one or more stops positioned to restrict longitudinal movement of the second proximal end portion and/or the second distal end portion.

21. A neuromodulation method, comprising:
advancing an elongate shaft of a neuromodulation catheter toward a treatment location within a body lumen of a human patient while a neuromodulation element of the catheter is in a low-profile delivery state;
independently expanding a series of bow springs of the neuromodulation element one at a time in a distal-to-proximal sequence as the neuromodulation element transitions from the delivery state to a deployed state at the treatment location;
energizing electrodes and/or transducers carried by the bow springs to modulate one or more nerves of the patient while the neuromodulation element is at the treatment location and in the deployed state.

22. The neuromodulation method of claim 21 wherein:
advancing the shaft includes advancing the shaft while the neuromodulation element is disposed within a sheath; and
independently expanding the bow springs includes retracting the sheath relative to the neuromodulation catheter and/or advancing the neuromodulation catheter relative to the sheath so as to allow the bow springs to resiliently urge the electrodes and/or the transducers toward an inner surface of a wall of the body lumen.

23. The neuromodulation method of claim 21 wherein independently expanding the bow springs includes urging the electrodes and/or the transducers into contact with an inner surface of a wall of the body lumen at a series of longitudinally and circumferentially spaced-apart contact regions.

24. The neuromodulation method of claim 23 wherein the contact regions are disposed along a helical path.

\* \* \* \* \*